United States Patent [19]

Alais

[11] 4,351,038

[45] Sep. 21, 1982

[54] ULTRASONIC EXAMINATION AND IMAGING

[75] Inventor: Pierre Alais, Dampierre, France

[73] Assignee: Agence Nationale de Valorisation de la Recherche (ANVAR), Dampierre, France

[21] Appl. No.: 221,421

[22] Filed: Dec. 30, 1980

[30] Foreign Application Priority Data

Dec. 31, 1979 [FR] France .............................. 79 32097

[51] Int. Cl.³ ............................................. G01S 15/89
[52] U.S. Cl. ...................................... 367/105; 73/626; 367/7; 367/138
[58] Field of Search ....................... 367/7, 87, 105, 138; 73/626

[56] References Cited

U.S. PATENT DOCUMENTS

| | | | |
|---|---|---|---|
| 4,117,446 | 9/1978 | Alais | 367/7 |
| 4,119,938 | 10/1978 | Alais | 367/105 |
| 4,234,940 | 11/1980 | Iinuma | 367/105 |
| 4,253,338 | 3/1981 | Iinuma et al. | 367/105 X |

*Primary Examiner*—Richard A. Farley
*Attorney, Agent, or Firm*—Larson & Taylor

[57] ABSTRACT

An ultrasonic imaging device comprises transducers distributed along a line and operable at a frequency f. A generator delivers electrical pulses to time delay means which provide, in response to each electrical pulse, a plurality of low level pulses delayed by increased time delays in a number lower than the number of transducers. The distribution of the time delays between the transducers is stored in memory means and corresponds to focusing at a point located at a predetermined distance from the line. A plurality of amplifiers are each associated with an individual one of the transducers and deliver an energizing pulse to the associated transducer in response to a particular one of the low level pulses appearing on an associated channel of a bus line which is selected by the memory.

15 Claims, 10 Drawing Figures

ULTRASONIC EXAMINATION AND IMAGING

BACKGROUND AND SUMMARY OF THE INVENTION

The present invention relates to electronic ultrasonic sounding for exploring a piece of body to be examined, particularly although not exclusively in depth, i.e. in B echography or B scan.

Inventor's U.S. Pat. No. 4,119,938 and French Pat. No. 2,292,978 disclose and claim an ultrasonic imaging device comprising N elementary transducers distributed at equal intervals along a displacement line and capable of operating at ultrasonic frequency f, a generator (or receiver) associated with the transducers by dephasing means, and means for storing the distribution over n successive elementary transducers (n being an integer less than N) of the phases corresponding to focusing at a given distance from the line for frequency f. Switching means connect a group of n transducers to the dephasing means and to the generator (or receiver) in accordance with said distribution. Then the group of n elementary transducers is shifted along said line at equal time intervals. The dephasing means are provided for giving phase shifts which are multiples of $2\pi/a$ (a being an integer less than n) and said storage means store the distribution of the phase shifts.

The device of that type described by way of example in French Pat. No. 2 292 978 uses the same number n of successive elementary transducers for reception and emission, with the same distribution, corresponding to several Fresnel zones associated with focusing at a desired distance and phase sampling uses two phases which differ from each other by $\pi$. The patent specification also contemplates a finer sampling, by using a number a of phases greater than 2. But it is then necessary to provide more complex switching means and emission and reception circuits ensuring phase shifts which are multiples of $2\pi/a$.

Another prior art device (U.S. Pat. No. 4,117,446) includes memory means and registers having a number of binary positions p times greater than that used in the device described in U.S. Pat. No. 4,119,938 and may provide a first Fresnel configuration of "lens" at emission-transmission and p−1 Fresnel configurations or "lenses" at reception, having different apertures and focal lengths. Switching of the latter lenses may be rapid enough to have optimum dynamic focusing. The term "dynamic focusing" designates a modification by jumps of the focal distance progressively as the echoes return so that at any moment the receiver configuration is optimum for receiving the echoes liable to be formed at the position occupied at the same time by an ultrasonic return echo.

In a particular embodiment described in U.S. Pat. No. 4,117,446, binary quantization of the phase is used, a quantization which has the merit of simplicity. For reducing the secondary lobes to an acceptable level, the emitting lens comprises a number $n_0$ of transducers less than the number n used at reception and corresponding to the first Fresnel zone only. As a counterpart, there is an attendant disadvantage: the resolution is decreased.

It is an object of the invention to improve upon the prior art techniques of ultrasonic examination and imaging, particularly, in that fine phase sampling is achieved with simple and relatively low cost means; it is another object to provide improved focusing upon transmission as well as upon reception without secondary lobes of a prohibitive level.

According to an aspect of the invention, there is provided a device for ultrasonic imaging, comprising: n elementary transducers distributed at equal intervals along a predetermined line and operable at ultrasonic frequency f; a generator of electrical pulses; and time delay means operatively associated with said generator for delivering, in response to each electrical pulse from said generator, a plurality of low level pulses delayed by increased time delays $\tau, \ldots, (a-1)\tau$, ($\tau$ being a predetermined time delay) on different channels, a being an integer less than n. Means are provided for storing a distribution of said a time delays between said n transducers corresponding to focusing of transmitted ultrasonic energy at a point located at a predetermined distance from said line at frequency f. A plurality of amplifiers are each associated with an individual one of said transducers for delivering an energizing pulse to the associated transducer in response to one of said low level pulses appearing on an associated channel selected by the storing means.

Since the lines and the means for controlling the amplifiers have not to transmit the power necessary for energizing the transducers (which is supplied by the amplifiers), the amplifiers may be controlled by analog multiplexers, which now exist in the form of inexpensive integrated circuits.

According to another aspect of the invention, the switching means may comprise, for each transducer, a supply amplifier and a multiplexer for controlling the amplifier by means of a low-level signal coming from one of the a lines or channels of a general bus. Each line or channel receives R pulse signal from the emitter (transmitter) through means giving relative delays which are multiples of $2\pi/a$.

According to a further aspect of the invention, which relates to reception rather than transmission, a multiplexer (which will typically be used also at transmission) is associated with each transducer and is connected, through a common bus, to a channels on which phase-shift means are located. A circuit is provided for summing the analog reception echoed signals. Each multiplexer may comprise a multi-bit control input connected to a respective stage of a shift register associated with a clock for moving said stored distribution along the register, whereby electronic scanning may be achieved if the n transducers which are simultaneously in operation are part only of a greater number N of transducers evenly distributed along a scanning line.

This arrangement provides the advantages already mentioned in U.S. Pat. No. 4,117,446, however in combination with a much improved fine sampling favorable to a very high resolution.

Practically, a resolution close to the maximum is reached by using modulo $2\pi/8$ sampling of the phase; it requires a bus line having eight channels associated with the multiplexers. The same multiplexers convey, in one direction, the signals for controlling the amplifiers (logic control at a 5 volt level for example) and, in the other direction, the reception signals provided by the transducers and brought up to a suitable level by means of a linear amplifier.

According to yet another aspect of the invention, there is provided an electronic translation ultrasonic sounding device comprising N elementary transducers distributed at equal intervals along a translation line and capable of operating at an ultrasonic frequency f, a generator (or receiver) associated with the transducers by phase-shift means, and means for storing the distribution over n elementary transducers (n being less than N) of the phases corresponding to focusing at a given distance from the line for frequency f, as well as switching means for connecting a group of n transducers to the phase-shift means and to the generator (or receiver) depending on said distribution, then in shifting at equal intervals of time, the group of n elementary transducers along said line. The phase-shift means are provided for giving a different phase shifts and the storage means for storing the distribution of the a phase shifts between the n transducers. The switching means comprise, for each transducer, a supply amplifier and a multiplexer for controlling the amplifier by means of a low-level signal coming from one of the a channels of a general bus line, these channels being each associated with one of the phase-shift means.

The a phase shifts may be distributed evenly; but in some cases it is more advantageous to have different intervals, for example to take into account the variation of the slope of the representative curve of the phase depending on the distance to the center of the group of n transducers. The phase-shift means may themselves be formed by very different elements, such as phase-shifters, delay lines and, at emission, shift registers.

To ensure dynamic focusing, it is sufficient to control the multiplexers, not only at emission but also for the p−1 successive reception periods, by means of N outputs from a register which transit words of b bits on pN positions, the word b causing, for a first value, blocking of the multiplexer (transducer not supplied) and, for the others, opening of the multiplexer with selection of one of the a channels of the bus line.

An additional result sought by the invention in the case of dynamic focusing consists in minimizing the extent of the switching noise engendered during focal distance changes, which noise risks being greater than the weak echoes received, without introducing any frame disturbance harmful to the quality of the image.

To this end, the invention provides a device which alternates two groups of complementary focal zones.

The invention will be better understood from reading the description which follows of devices which form particular embodiments thereof, given by way of non-limiting examples.

SHORT DESCRIPTION OF THE DRAWINGS

Figure 6A:
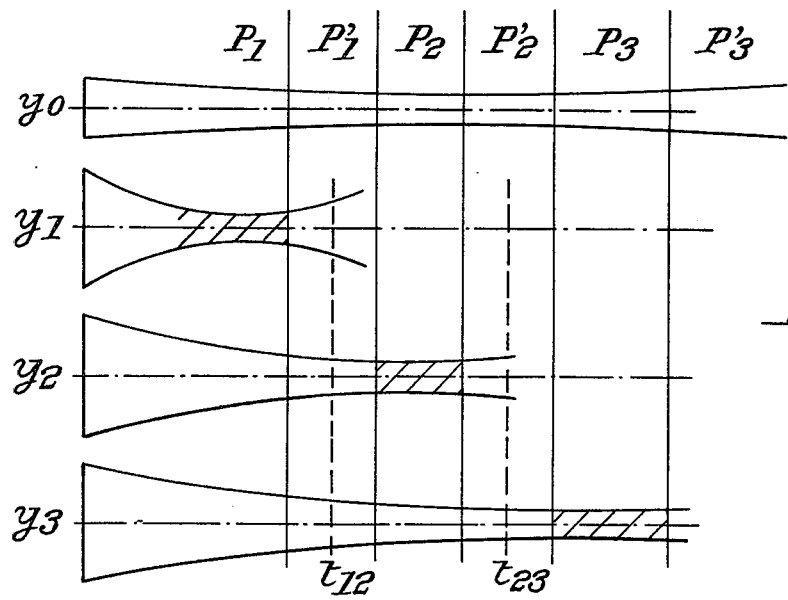
FIGS. 6a and 6b are diagrams illustrating the principle of dynamic focusing in alternate zones from one frame to the next, in the particular case of dynamic focusing in two times three zones at reception.
Figure 6B:
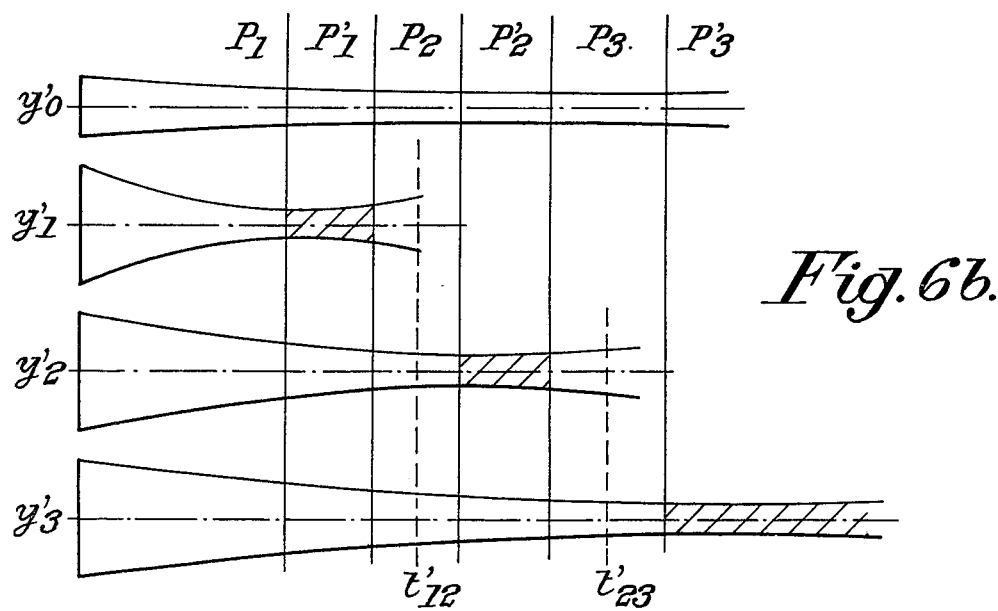
Figure 7A:
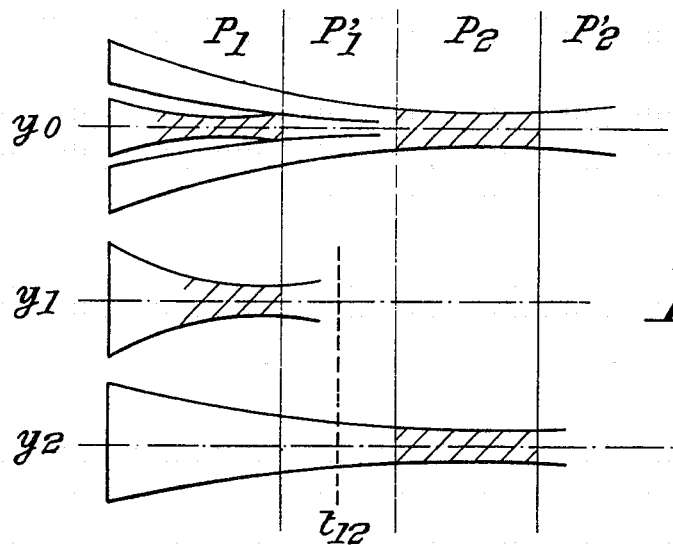
Figure 7B:
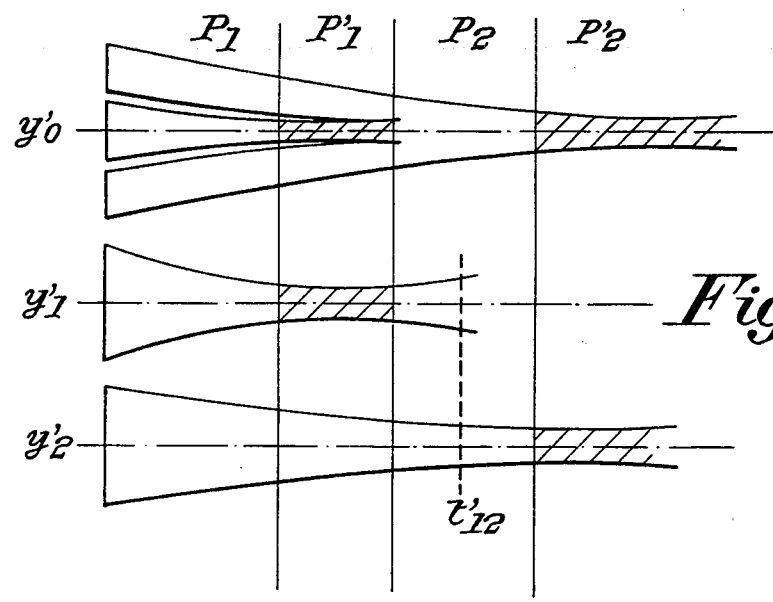

FIGS. 7a and 7b, similar to FIGS. 6a and 6b, illustrate a bifocal concentration at emission associated with dynamic focusing in two times two zones at reception.

As mentioned in U.S. Pat. No. 4,119,938, it is possible to achieve focusing at emission or at reception along a line transverse to a group of n transducers distributed in a direction Ox, at a distance y from the right-hand segment on which the n elementary transducers are distributed, by using a phase distribution between the transducers which simulates the phase-shift distribution $\phi$ as a function of the abscissa x from the center O which supplies focusing at the point situated at distance y. This phase shift is given by the formula:

$$\phi = \frac{\pi x^2}{\lambda y}$$

where $\lambda$ is the wavelength of the ultrasounds in the propagation medium.

Figure 1:
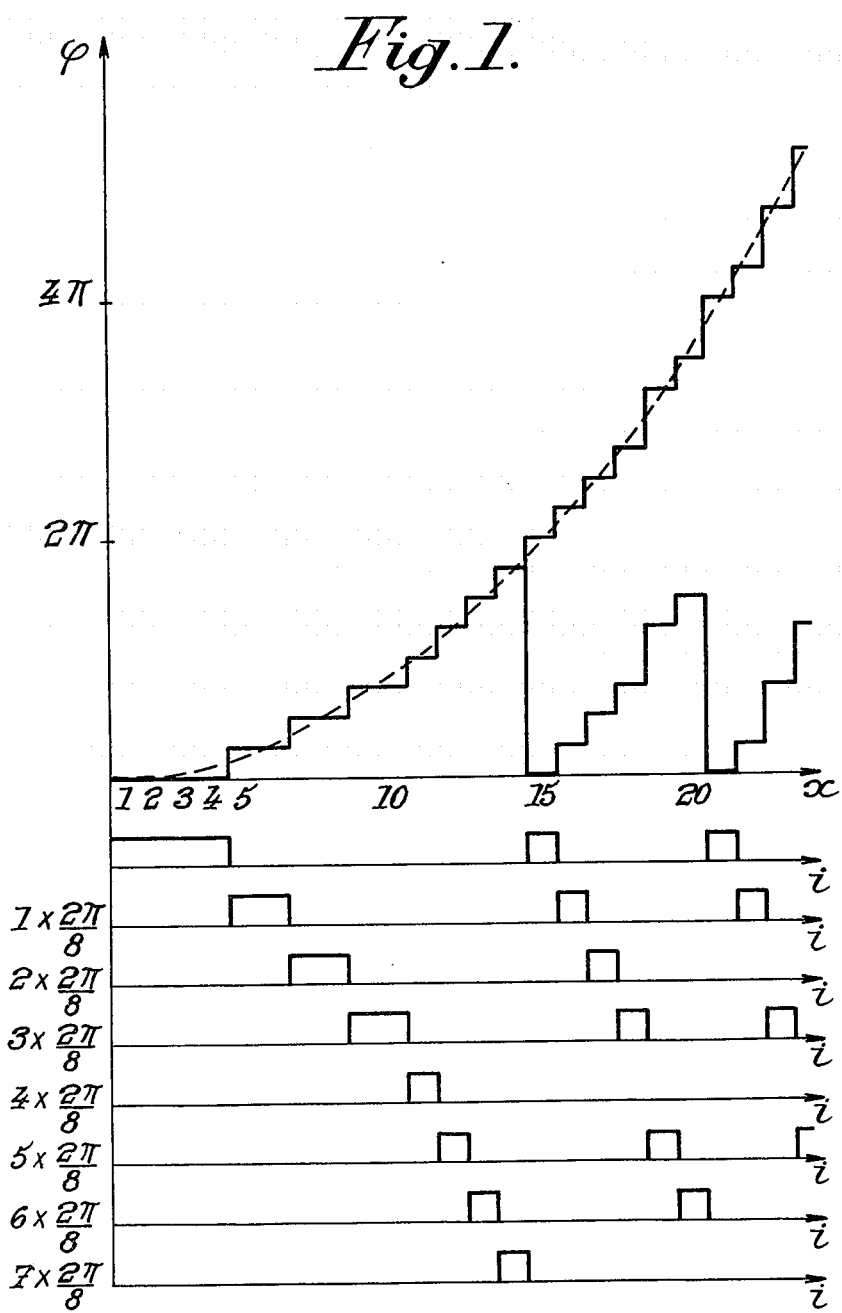
FIG. 1 is a diagram showing the distribution in eight phases, differing by $2\pi/8$, to be provided over transducers distributed in a direction Ox to ensure focusing at a given distance y.

A rough approximation is obtained by using a binary quantization phase distribution, as described by way of example in U.S. Pat. No. 4,119,938. But a finer approximation of the above relation may be obtained by effecting sampling at a levels, a being greater than 2. By way of example, the top part of FIG. 1 shows sampling at a=8 levels, the phase state of each of the transducers being chosen as the closest $2\pi$ modulo to the value of the phase reached by the Fresnel law $\phi$ (x) at the center of the elementary transducer considered. With the theoretical distribution of the phase indicated with a broken line in FIG. 1, the actual distribution of a phases between the transducers is that indicated by the staircase curve.

Figure 2:
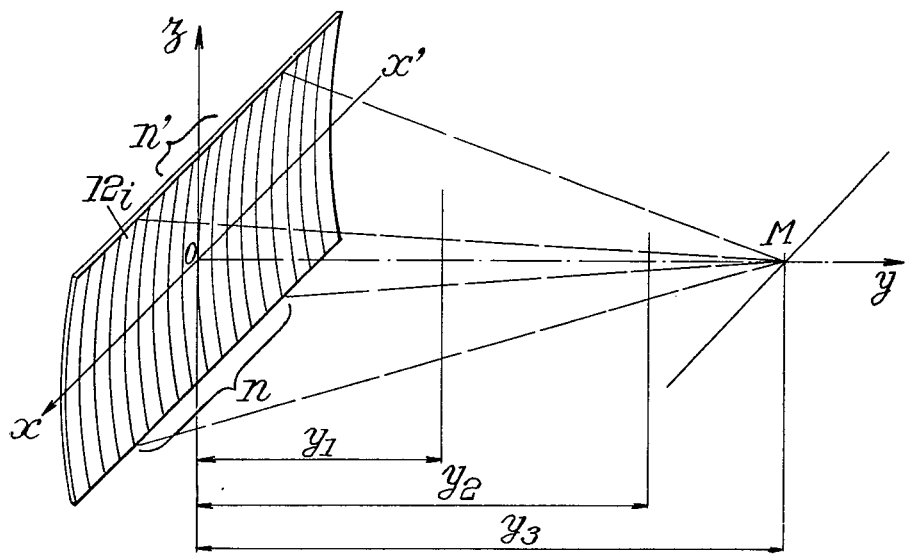
FIG. 2 shows a possible arrangement of N elementary transducers for implementing the invention.

The distribution shown in FIG. 1 may be obtained by using a system of transducers of the kind shown schematically in FIG. 2. This system comprises N transducers $12_1, \ldots 12_i, \ldots, 12_N$ of which will be assumed that n are used at each reception. The transducer system ensures geometric focusing, obtained by disposing the elementary transducers along a cylindrical surface whose center is at a distance from the system chosen as a function of the contemplated application, for example about 10 cm for medical imaging. The system of FIG. 2 comprising a total number N of elementary transducers greater than n (for example N=3n), provides electronic scanning in direction x'x in addition to focusing by an electronic process, either at a single distance or, as will be seen further on, at several successive distances $Y_3$, $Y_2$, $Y_1$ to ensure dynamic focusing.

Figure 3:
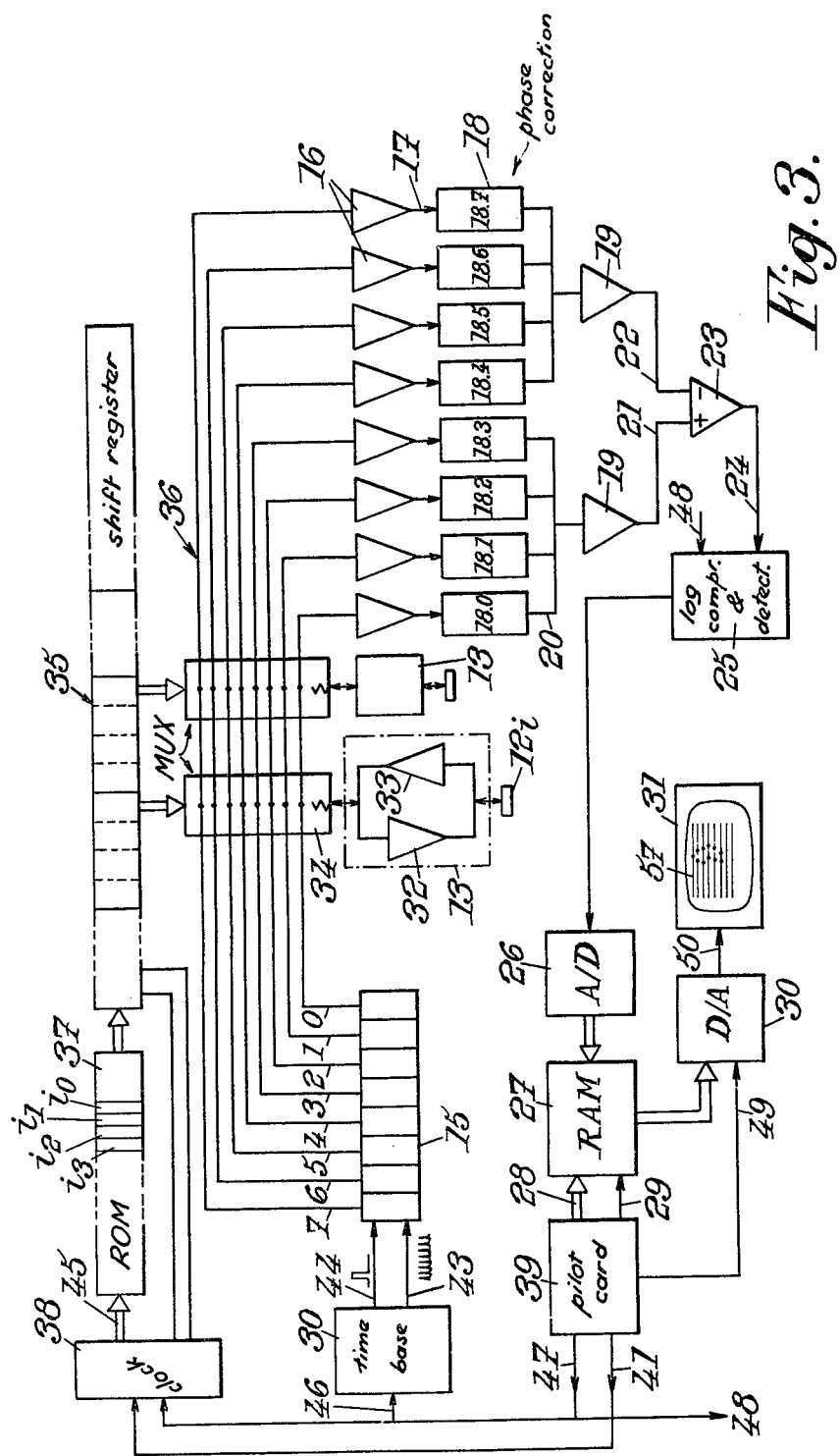
FIG. 3 is a simplified drawing of a circuit usable with the network of transducers of FIG. 2 for implementing the invention.

The electronic circuit shown schematically in FIG. 3, in which a a single elementary transducer $12_i$ is shown with its associated amplifier-receiver circuit 13, is intended to provide approximation of the Fresnel curve by use of eight phase levels, reception using n elementary transducers with dynamic focusing at p−1 distances and emission using a number n' of transducers less than n (FIG. 2).

For each of the focusings to be provided, the circuit of FIG. 3 will have to energize n transducers $12_i$ with a well-determined phase distribution. To achieve the distribution shown at the top part of FIG. 1, the circuit will apply for example an energization pulse without phase shift to transducers Nos. 1, 2, 3, 4, 15 and 21; it will cause a phase shift of $2\pi/8$ of the signal applied to transducers Nos. 5, 6, 16 and 22 and so on, as shown on the lines in the lower part of FIG. 1.

The circuit shown in FIG. 3 is provided for association with a system of N transducers $12_1, \ldots, 12_i, \ldots, 12_N$, excitable by pulses. The energization and amplification circuit 13 associated with each transducer $12_i$ comprises a threshold type nonlinear amplifier 32 capable of delivering the high level pulse required from the signal from a control logic, a protected linear amplifier 33 conveys back the reception signals due to the echoes. The amplitude of the amplifier output is limited to prevent self-oscillation of the loop thus formed.

Switching means associated with the circuit 13 of each transducer $12_i$ have only weak signals to transit, typically 5 volts at most at emission, of the order of 100 mV at reception. They may be quite simple consisting for example of an analog multiplexer 34 having a channels. In the case illustrated where a=8, inexpensive C-MOS (complementary MOS) multiplexers may be used, for example of type CD 4051, which can only transmit logic signals, whereas the amplitude of the voltage oscillation at the level of the transducer, typically ceramic, may exceed 100 V at emission.

All multiplexers 34 are disposed on the same bus 36 having a channels (eight channels in the embodiment illustrated) and are controlled by a shift register 35. The control by the register must allow each transducer to be connected to any one of the eight channels, marked 0, 1, ..., 7 in FIG. 3, of the bus 36 or the transducer to be separated. Consequently, each multiplexer 34 must be controlled by a four-bit word, three for selection of the channel, and one for isolating the transducer or connecting it.

Register 35 has accordingly four parallel channels. Considering the number of register positions which will be generally required (for example 640 if N=160 and p=4), register 35 will generally be formed by several elementary registers disposed in cascade. A series of CD 4006 four-bit registers with four parallel channels may in particular be used.

The programming of the p=4 distributions to be provided and their circulation in register 35 may be effected by means similar to those described in French Addition No. 2 355 288 and the corresponding U.S. Pat. No. 4,117,466 to which reference may be made. The a=4 phase distributions to be provided during an exploration in depth using n successive elementary transducers are displayed in a read-only memory, advantageously reprogrammable, capable of containing p×n four-bit words. In the case where a network of N=160 transducers is used, there may be adopted, for the "electronic lenses," a maximum aperture corresponding substantially to a third of the network, i.e. n=64.

With the read-only memory 37 there is associated a clock 38 which transfers in sequence the four-bit words from the read-only memory 37 into register 35. The transfer of the four bits of the same word is effected simultaneously on receipt of a signal transmitted by the clock over four channels 45. Clock 38 drives at the same time the clock input of register 35. It can be seen that, as already described in U.S. Pat. No. 4,117,466, passing over from the configuration corresponding to the emission ($i_0$ for the transducer of order i) to the first reception configuration, corresponding to word $i_1$ for example, is effected in response to a signal from clock 38 which activates at one and the same time memory 37 over 45 and register 35. Thus, the dynamic focusing is made simple, providing that the switching noises are obviated at the level of multiplexers 34, as will be seen further on. Passing over from one firing line (Oy in FIG. 2 for example) to the next firing line, shifted by a distance corresponding to the space between two transducers, is effected in four shots of clock 38.

The "emission" part of the circuit uses the fact that the phase advance is equivalent to a time advance, a phase difference of $2\pi/8$ corresponding to a time shift equal to T/8, T being the period of the ultrasounds emitted. This "emission" part comprises a card 39 comprising a clock having a gate input 46 and two outputs 43 and 44. Output 44 is provided for supplying a control signal for transiting in a register 15 having eight binary positions, each associated with one of the channels 0 to 7 of the bus line 36. Card 30 is provided for supplying at its output 43, in response to the gate signal applied to input 46, a sequence of eight short pulses, of about 1 microsecond for example, at a frequency equal to eight times the nominal frequency of the ultrasonic signals.

Thus the control signal appears first of all on channel 7 of bus line 36 then on channel 6 and so on up to channel 0. The control signal appears on channel 0 with a delay of one ultrasonic period with respect to the control signal at output 44.

Clocks 38 and 30 are connected to a pilot card 39 which ensures sequencing of the whole operation. This card is provided for delivering, at one output 41, a signal for controlling clock 38 at the beginning of each complete sequence of operation. This signal will be called "frame synchronization." Card 39 delivers furthermore, at another output 47, a signal which will be called "line synchronization" applied to clocks 38 and 30.

The "reception" part of the circuit of FIG. 3 comprises, for each channel of the bus line, a current-voltage amplifier 16 capable of supplying, at its output 17, a voltage proportional to the current injected by the corresponding channel, while maintaining the potential of this channel at a very low value. The current injected by the line reproduces the sum of the signals supplied by the transducers connected to the channel through resistances of the corresponding multiplexers 34.

Downstream of each amplifier 17 there is placed a corresponding phase-correction circuit 18. Circuits 18 are for example formed from conductances combining inductances, resistors and/or capacitors selected to provide a phase shift of from $-\pi/2$ to $+\pi/2$ (except for use in negative resistors implying active components). This phase-shift range is sufficient by effecting subsequently a four-to-four addition of the outputs 20 of the inductances, then an additional phase shift of $\pi$ (which is the same as an inversion) on the resultant of one of the sets of four outputs.

In the embodiment illustrated in FIG. 3, we will take for example as reference $\gamma$ the conductance 18-0 associated with channel 0, which will be formed by a series circuit of an inductance coil and a resistor. The other conductances 18-0 to 18-7 will then have to have respectively the values $\gamma \exp (j\pi/4)$, $\gamma \exp (j\pi/2)$, $\gamma \exp (j\cdot 3\pi/4)$. They will be formed respectively by a pure resistor, by a resistor and a capacitor in series and by a capacitor. The currents appearing at the outputs 20-0, 20-1, 20-2 and 20-3 are summed by an amplifier 19 which provides at its output 21 a voltage representative of the sum, with phase correction.

Conductances 18-4 to 18-7 are formed respectively as conductances 18-0 to 18-3 and the currents are converted by a second amplifier 19 into a voltage 22 which is applied to the "negative" input of a differential amplifier 23, which is equivalent to an additional phase shift of π with respect to potential 21, applied to the "plus" input of the same amplifier 23.

The signal resulting from the summation, corrected in phase, is thus obtained at the output 24 of differential amplifier 23.

This signal then undergoes conventional logarithmic compression, detection and gain correction in depth, in a complex conventional-type circuit 25. Circuit 25 receives, at one control input 48, the line synchronization signal from pilot 39. The output of circuit 25 is connected to an analog-digital converter 26 whose output, for example a four-bit output allowing quantization at sixteen levels, drives an addressable read-write digital memory 27, having a capacity sufficient to be able to store a complete image. Memory 27 is also provided with an input 28 for addressing by the pilot 39 and a "write" input 29. It will generally be formed from RAM memories whose reading cycle may be addressed and controlled independently of the writing cycle. In the case discussed above of N=160 transducers, memory 24 will then have to have a capacity of at least $2.5 \times 160$ four-bit words and will allow the stored data to be read in accordance with a line-frame standard for driving a conventional video monitor 31, with raster scan, or a magnetoscope for recording and filling the views. Reading is effected permanently by a circuit 30 comprising a digital-analog converter and a synchronization circuit which receives the line and frame synchronization signals from pilot 39 at one input 49 and supplies a composite video signal at output 50.

Figure 4:
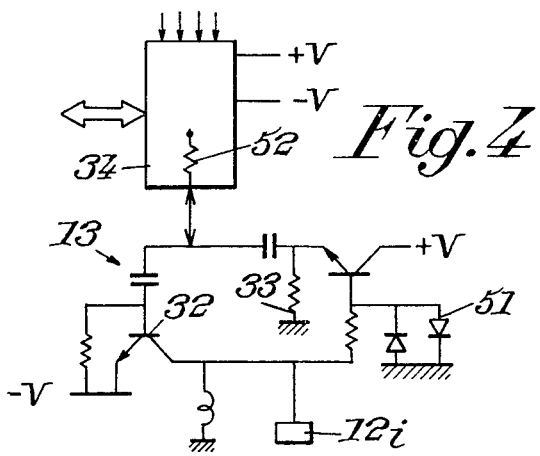
FIG. 4 shows a particular embodiment of the energization and amplification circuits associated to a transducer.

Circuit 13 associated with each transducer may have the constitution shown in FIG. 4. The threshold emission amplifier 32 and the reception amplifier each comprise a single transistor. Diodes 51 allow the output amplitude of amplifier 33 to be limited. A source of 30 V and $-V$ voltages supplies the emission power necessary, which does not then have to transit through resistor 52 (75Ω for example) of the multiplexer. It can be seen that the assembly found in each multiplexer is very simple and inexpensive.

Figure 5A:
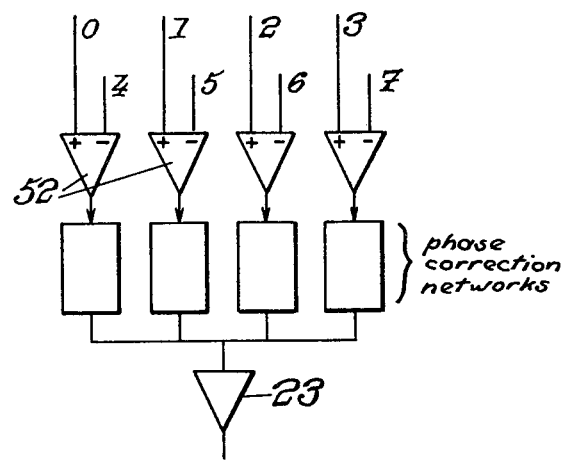
FIGS. 5a and 5b show two possible variations of the phase-shift means incorporated in the reception circuit, forming phase correctors.
Figure 5B:
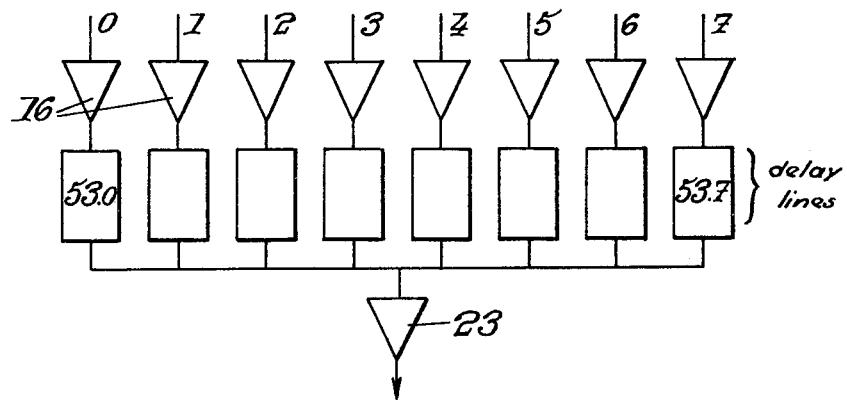

The reception circuit may have numerous embodiments some of which are shown in FIGS. 5a and 5b.

In the case of FIG. 5a, the eight amplifiers 16 of FIG. 3 are replaced by four differential amplifiers 52, which allows the number of conductances to be reduced to four, which have respectively the values $\gamma$, $\gamma \exp(j\pi/4)$, $\gamma \exp(j\pi/2)$ and $\gamma (j \cdot 3\pi/4)$ for the rated ultrasonic frequency. The same circuit may be used by replacing the inductances with delay lines, providing respective delays of 3 T/8, 2 T/8, T/8 and 0. The use of delay lines may be advantageous when very damped transducers are used for their characteristics are well-adapted to Fresnel focusing at emission and at reception of short wideband signals such as can be delivered by such transducers.

Finally, FIG. 5b uses, downstream of the current-voltage amplifiers 16, delay lines 53-0 to 53-7 which provide delays of 7 T/8, 6 T/8, ... T/8 and 0 at the rated ultrasonic frequency. Like the circuit of FIG. 5a, that of FIG. 5b does away with the current-voltage amplifiers 19 of FIG. 3.

As was pointed out above, it is desirable to remove the effects of switching noises. This result may be attained by using a process whose principle will be explained with reference to FIGS. 6a and 6b.

FIG. 6a shows the type of the focusing obtained at emission with n' transducers (line $j_0$) and focusings at distances $y_3$, $y_2$ and $y_1$ obtained during the three reception steps with n transducers and different phase distributions. The observation zone may be cut up into zones of finite depth $P_1$, $P_2$, $P_3$ containing respectively pseudo focal points at distances $y_1$, $y_2$ and $y_3$, sandwiched with other zones $P'_1$, $P'_2$ and $P'_3$. By a suitable choice of the phase distributions of the transducers, focusing may be obtained at emission at distance $y'_0$ and at reception at distances $y'_1$, $y'_2$ and $y'_3$ such that the focal points are respectively in zones $P'_1$, $P'_2$ and $P'_3$.

For removing the switching noises when the first configuration (FIG. 6a) is used, it is sufficient to inhibit writing during the time intervals which correspond to the echo returns from reception zones $P'_1$ and $P'_2$, in which intervals are situated switching times $t_{1-2}$ and $t_{2-3}$. Provided that a second set of four configurations (or more generally of p configurations) is provided and providing that it is used alternately with the first one, each during a complete frame, it will be possible, during one frame out of two, to inhibit writing during the time intervals which correspond to the echo returns from zones $P_2$ and $P_3$, in which intervals are situated switching times $t'_{12}$ and $t'_{23}$. To have a complete image in two frames without juxtaposition, inhibition will be in fact effected in zones $P'_1$, $P'_2$ and $P'_3$ during one frame, in zones $P_1$, $P_2$ and $P_3$ during the next one. Thus, memory 27 is permanently totally written and reading thereof provides a perfectly continuous image where six zones join up without any visible discernable effect, with focusing and optimum resolution at any depth.

FIGS. 7a and 7b show another variation of dynamic focusing with suppression of the switching noises. This variation uses an emission with double focusing, but only two reception zones, $P_1$ and $P_2$ on one frame, $P'_1$ and $P'_2$ on the next one. Here again, the complete image is reconstituted in two frames. But, in addition, effective focusing is ensured not only at reception but also at emission.

Since operation of the device is clear from the preceding description and since it is moreover similar to that of the device described in U.S. Pat. No. 4,117,446, it will only be briefly described.

It will first of all be assumed that the device is provided for ensuring, at emission, pseudo-focusing at a distance of about 10 cm, by using a number $n'(<64)$ transducers $12_i$ and, at reception, dynamic focusing at three successive distances using each time sixty-four transducers, the focusing distances being the same at each frame. In other words, there will first of all be described an operation not using the system for eliminating switching noises shown schematically in FIGS. 6 and 7.

Initially, the four phase configurations corresponding, the first one to the emission, the others to the three distances $y_1$, $y_2$ and $y_3$, are stored in the read-only memory 37. The pilot card 39 must first of all control clock 38 so as to load into register 35 a fraction of the four focusing configurations sufficient for the first firing to be sufficiently accurate. In practice, half of the electronic reception "lenses" will be loaded, so four times thirty-two four-bit words. The pilot then causes the emission, by clock 38, of four times thirty-two=a hundred and twenty-eight shots, in response to a pulse provided at output 41 (frame synchronization).

The first "firing line" is then placed facing transducers $12_1$.

In response to a line synchronization signal delivered at its output 47 by the pilot card 39, clock 30 provides a control signal at its output 44 and a train of eight pulses at a frequency equal to eight times the nominal frequency of the ultrasounds, of the order of 4 MHz in general, at output 43. The control signal thus circulates in register 15. It appears, at intervals T/8, successively on channels 7 to 0.

With multiplexers 34 connected at that time to positions of register 35 containing the emission configuration, the n' transducers serving for emission are connected by multiplexers 34 to lines 0 to 7 corresponding to the emission configuration.

Clock 38, still controlled by a pulse from pilot card 39, then sends an advance pulse. Multiplexers 34 will then connect half of the sixty-four transducers normally used to channels 0 to 7 in a configuration corresponding to reception focusing at distance $y_1$. On reception of an additional pulse from pilot 39, there will be reception with focusing at distances $y_2$ and $y_3$. Clocks 38 and 30 may furthermore be provided for ensuring the complete operating sequence along a given firing line on reception of a single frame synchronization pulse from output 47.

The reception signals, processed as has already been described, are stored in memory 27, synchronization being assured by circuit 25 which also receives the line synchronization pulses. Writing is effected on television monitor 31 in the form of bright dots representing the echoes on a scanning line, the depth of the echo being shown by the distance from the beginning of the scan (B-scan).

The next line synchronization signal shifts by one the transducers which will be connected by the multiplexers to the emission configuration. The firing line is then placed facing transducers $12_2$. The sequence defined above is reproduced.

Scanning finishes when there only remains in register 35 half of the reception "electronic lenses." The image is then shown on a complete frame of television monitor 31.

It is not necessary to describe here the modifications of operation caused by the use of a switching noise elimination system. In practice, the modifications required are limited to the addition of a second read-only memory 37 in parallel with the first one, the contents of the two memories being then loaded alternately into register 35.

I claim:

1. A device for ultrasonic imaging, comprising:
    n elementary transducers distributed at equal intervals along a predetermined line,
    a generator of electrical pulses,
    time delay means operatively associated with said generator for delivering, in response to each electrical pulse from said generator, a plurality a of a low level control pulses delayed by different fixed time delays on different channels, a being an integer,
    means for storing a distribution of said a time delays between said n transducers corresponding to focusing of transmitted ultrasonic energy at a point located at a predetermined distance from said line,
    a plurality of amplifiers each associated with an individual one of said transducers for delivering an energizing pulse to the associated transducer in response to one of said low level pulses appearing on an associated channel selected by said storing means,
    a plurality of analog multiplexers each associated with a corresponding one of said amplifiers, and a bus operatively associated with said time delay means and having a plurality a of individual lines each arranged to receive a different one of said low level pulses and to control at least one said amplifier connected thereto through means of the associated multiplexer, the said associated multiplexer being controlled in turn by switching means for achieving said distribution.

2. A device according to claim 1, wherein said different fixed time delays have values $\tau, 2\tau, \ldots, (a-1)\tau$, wherein $\tau$ is a predetermined time delay and said a individual lines are connected through phase shifting means to summing means for summing electrical signals delivered by said transducers in response to ultrasonic echoes.

3. A device according to claim 2, wherein said phase shifting means comprises two sets having a/2 conductances supplying a step-by-step variation of a phase shift at intervals of $2\pi/a$, each said conductance being associated with one of said individual lines, and said summing means comprising two amplifiers each driven by the a/2 conductances of the same set and a differential amplifier which receives the outputs of the two summing amplifiers on inputs of opposite polarities.

4. A device according to claim 3, wherein the summing amplifiers are of the current-voltage type.

5. A device according to claim 2, wherein the phase shifting means comprises a/2 conductances supplying different phase shifts separated by intervals equal to $2\pi/a$, each conductance being associated with two of said individual lines by a differential current voltage amplifier whose inputs of opposite polarities are connected to respective ones of said two lines.

6. A device according to claim 1, wherein the storage means are provided for achieving focusing at a first distance during transmission of ultrasonic energy by said transducers and p−1 successive focusings at reception, p being an integer greater than 1.

7. A ultrasonic imaging and scanning device comprising:
    N elementary transducers distributed at even intervals along a scanning line and capable of operating at ultrasonic frequency f upon receipt of an energizing pulse,
    an electrical pulse generator,
    means for storing a distribution over n successive elementary transducers (n being an integer less than N) of the time delays $\tau, \ldots, (a-1)\tau$ corresponding to focusing at a predetermined distance from said line, $\tau$ being the time delay corresponding to a phase shift of $2\pi/a$ where a is an integer less than n,
    time delay means operatively connected to said generator and to a lines constructed to supply, over said a lines, pulses delayed by predetermined and fixed times $0, \tau, \ldots, (a-1)\tau$ responsive to a pulse from said generator,
    and power amplifiers each associated with a separate one of said transducers and with switching means for delivering an energizing pulse to the associated transducer upon occurrence of a pulse on a respective one of said lines selected by the storing means.

8. A device according to claim 7, wherein said switching means comprises an analog multiplexer associated with each transducer and power amplifier.

9. A device according to claim 1 or 7, wherein a is equal to eight.

10. An ultrasonic imaging and scanning device with electronic scanning comprising: N elementary transducers distributed at equal intervals along a translation line and capable of operating at ultrasonic frequency f when energized by an electric power pulse; a generator of low level electrical control pulses; time delay means connected to receive said electrical control pulses one at a time, means for storing the distribution on n successive elementary transducers (n being less than N) of the time delays corresponding to focusing at a predetermined distance from the line for frequency f; and switching means for connecting a group of n transducers to the time delay means and to the generator in accordance with said distribution, then for shifting, at equal time intervals, the group of n elementary transducers along said line, said time delay means being provided for supplying a different predetermined time delays (a being an integer less than n) on a respective channels of a general bus and said storage means storing the distribution of the a phase shifts between the n transducers, wherein the switching means comprise a power amplifier individually associated to each transducer and an analog multiplexer for controlling said amplifiers by said low level control pulse from one of said a channels.

11. A device as claimed in claim 10, wherein said storage means are provided for achieving focusing at a first distance during emission and p−1 successive focusing at reception, p being an integer greater than 1.

12. A device as claimed in claim 11, wherein said storage means comprise a shift register having pN positions, each position for containing a binary word having a sufficient number of bits for causing the analog multiplexer associated with each transducer amplifier to either separate the amplifier from the bus or to connect it to a predetermined one of the a channels.

13. A device as claimed in claim 12, wherein the storage means comprise at least one read-only memory with pn positions each adapted to contain a multi-bit word having a number of bits corresponding to that of the shift register, said read-only memory being provided for storing, in each position, that one of the a time delays with which the corresponding transducer is to be connected to the generator.

14. A device for ultrasonic imaging comprising:
a plurality of transducers distributed at equal intervals and operating at frequency f;
a bus having a predetermined number a of signal channels, a being a predetermined integer;
a generator for delivering individual control pulses;
delay means for delivering, in response to each said control pulse, a plurality of delayed low level control signals at predetermined time intervals on said channels in succession, said time intervals corresponding to focusing at a predetermined distance from said transducer;
a plurality of analog multiplexers each associated with one of said transducers and with said bus;
storage means for controlling said multiplexers according to a stored distribution whereby each of said multiplexers is controlled to connect a predetermined one of said channels to the associated transducer through a transmission power amplifier for transmission of a ultrasonic signal and for return of the corresponding echoed signal independently of said transmission power amplifier;
and phase shifting and summation means connected to said bus line for delivery of an imaging signal.

15. A device according to claim 14, wherein said delay means comprises a register connected to receive said control pulses on a serial input and successive binary positions connected to respective ones of said channels.

* * * * *